United States Patent
Kong et al.

(10) Patent No.: US 10,444,131 B2
(45) Date of Patent: Oct. 15, 2019

(54) EVALUATING DEVICE OF FLEXURAL PROPERTY OF MATERIAL, AND EVALUATION METHOD USING THE SAME

(71) Applicant: SAMSUNG ELECTRONICS CO., LTD., Suwon-si (KR)

(72) Inventors: Hye Young Kong, Uijeongbu-si (KR); Bok Soon Kwon, Suwon-si (KR); Young Suk Jung, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 58 days.

(21) Appl. No.: 15/485,745

(22) Filed: Apr. 12, 2017

(65) Prior Publication Data
US 2018/0143119 A1    May 24, 2018

(30) Foreign Application Priority Data
Nov. 23, 2016    (KR) .................. 10-2016-0156328

(51) Int. Cl.
*G01N 3/20*    (2006.01)

(52) U.S. Cl.
CPC ....... *G01N 3/20* (2013.01); *G01N 2203/0012* (2013.01); *G01N 2203/0023* (2013.01);
(Continued)

(58) Field of Classification Search
CPC ............. G01N 3/20; G01N 2203/0435; G01N 2203/009; G01N 2203/0282; G01N 3/34;
(Continued)

(56) References Cited

U.S. PATENT DOCUMENTS 3,286,516 A * 11/1966 Post ...................... G01N 3/20
                                                 73/853
5,231,882 A *  8/1993 Bertele .................. G01N 3/32
                                                 73/852
(Continued)

FOREIGN PATENT DOCUMENTS

CN    204679351    9/2015
JP     03200047    9/1991
(Continued)

OTHER PUBLICATIONS

Ernests Auzins, et al., "Determination of stress-strain characteristics of thin polymer films on cylindrical specimens", Proceedings of the Estonian Academy of Sciences, (2012), vol. 61, No. 3, pp. 166-171.
(Continued)

*Primary Examiner* — Harshad R Patel
*Assistant Examiner* — Brandi N Hopkins
(74) *Attorney, Agent, or Firm* — Cantor Colburn LLP

(57) ABSTRACT

An evaluating device of a flexural property includes a holder, a body disposed on the holder and capable of being moved along with a length of direction of the holder, a clamp coupled to the body to be rotated on the body and fixing a first side of the specimen to be evaluated, and a pressing part disposed over the clamp and pressing a second side of the specimen opposite to the first side and disposed upper than the first side of the specimen to bend the specimen, and an evaluation method of a flexural property of the bent specimen using the same.

6 Claims, 16 Drawing Sheets

(52) U.S. Cl.
CPC ........... *G01N 2203/0075* (2013.01); *G01N 2203/028* (2013.01); *G01N 2203/0218* (2013.01); *G01N 2203/0282* (2013.01); *G01N 2203/0682* (2013.01)

(58) Field of Classification Search
CPC ............ G01N 3/08; G01N 2203/0617; G01N 2203/0682; G01N 27/22; G01N 2203/0629; G01N 2203/0264; G01N 2203/0023; G01N 2203/0005; G01L 5/0038; G01L 5/0057; G01L 5/0076
See application file for complete search history.

(56) References Cited

U.S. PATENT DOCUMENTS

| | | | | |
|---|---|---|---|---|
| 6,931,942 | B2 * | 8/2005 | Uhlik | G01N 3/20 73/853 |
| 8,544,340 | B1 | 10/2013 | Ardellean et al. | |
| 8,863,585 | B2 * | 10/2014 | Wang | G01N 3/34 73/812 |
| 2012/0067134 | A1 * | 3/2012 | Bell | G02F 1/1309 73/800 |

FOREIGN PATENT DOCUMENTS

| | | |
|---|---|---|
| JP | 07301588 | 11/1995 |
| JP | 10132702 | 5/1998 |
| KR | 100165028 | 3/1999 |
| KR | 1020090040937 | 4/2009 |
| KR | 1020150061956 | 6/2015 |
| WO | 2014171247 | 10/2014 |
| WO | 2015064819 | 5/2015 |

OTHER PUBLICATIONS

N. Fawcett, "A novel method for the measurement of Young's modulus for thick-film resistor material by flexural testing of coated beams", Meas. Sci. Technol., vol. 9, (1998), pp. 2023-2026.

Extended European Search Report—European Patent Application No. 17174821.3 dated Jan. 25, 2018, citing references listed within.

* cited by examiner

θ = 90°

$0 < \theta < 90°$ $90° < \theta < 180°$

EVALUATING DEVICE OF FLEXURAL PROPERTY OF MATERIAL, AND EVALUATION METHOD USING THE SAME

CROSS-REFERENCE TO RELATED APPLICATION

This application claims priority to Korean Patent Application No. 10-2016-0156328, filed on Nov. 23, 2016, and all the benefits accruing therefrom under 35 U.S.C. § 119, the content of which in its entirety is herein incorporated by reference.

BACKGROUND

1. Field

Embodiments of an evaluating device and an evaluation method of a flexural property, and more particularly, embodiments of an evaluating device and an evaluation method of properties of an evaluation subject material when being bent or folded are disclosed.

2. Description of the Related Art

Recently, interests in electronic devices capable of physically changing the appearances have been rising. Particularly, freely foldable or bendable electronic devices are being actively researched in various electronic technical fields.

There is an attempt to combine flexible display technologies into an electronic device having a display such as smart phone or TV. Examples of the flexible display technologies may include a bendable display capable of being freely bent, a rollable display capable of being rolled like a paper, or a foldable display capable of being completely folded.

An evaluation method of bending/folding behaviors for a substrate and an internal material of the flexible display generally includes a qualitative evaluation such as "count of bending number."

However, flexural properties of the flexible display may not be concisely apprehended only by the qualitative evaluation, so it is difficult to evaluate the reliability thereof.

In order to provide a sophisticated robot very similar to a human body, recently, artificial muscles mimicking biological muscles are being developed. For predicting kinetic characteristics of the artificial muscle, relationships between muscle contraction and muscle tension, hysteresis due to elastic motion/friction of muscle material, and the like, may be considered.

SUMMARY

A prediction of kinetic characteristics of artificial muscles is quasi-static by slowly carrying out with tension and shrinkage of the artificial muscles at a low speed, so it is impossible to predict a local and rapid flexural property as much as corresponding to biological muscles.

Thus, it is desired to select appropriate materials suitable for each of various electronic devices such as a flexible display, an artificial muscle, and an artificial body tissue and to provide a measurement means for quantitatively evaluating properties (flexural property) of the selected material in a simple method when the selected material is folded or bent.

An embodiment is to provide an evaluating device of a flexural property capable of quantitatively evaluating flexural property of a material in a simple method and an evaluation method.

According to an embodiment, a device for evaluating flexural property includes a holder, a body disposed on the holder and capable of being moved along with a length direction of the holder, a clamp coupled to the body to be rotated on the body and fixing a first side of a specimen to be evaluated, and a pressing part pressing a second side of the specimen which is opposite to the first side and disposed upper than the first side of the specimen to bend the specimen.

In an embodiment, the device for evaluating flexural property may further include a rotation axis penetrating the body and the clamp and inserted through the body and the clamp and a manipulating dial coupled to a terminal end of the rotation axis.

In an embodiment, an elongation direction of the rotation axis may be different from the length direction of the holder.

In an embodiment, an angle between the clamp and the body may be about 0 degree to about 180 degrees.

In an embodiment, the body may be disposed to be slid along with the length direction of the holder.

In an embodiment, a guide groove may be defined in the upper surface of the holder along with a length direction of the holder, and a moving member accommodated in the guide groove may be defined in the lower surface of the body.

In an embodiment, the device for evaluating flexural property may include a wire connected to each of the body and the pressing part and a pulley wired with wire.

A method of evaluating flexural property of the bent specimen using the device for evaluating flexural property includes:

using a thickness (h) of the bent specimen, a length (L") of a first arc connecting a first point with a second point which are different from each other and applied with principal stress corresponding to a half of the maximum principal stress applied to the bent specimen, a length (L') of a first straight line connecting the shortest distance between the first point and the second point, a curvature radius (ρ) of a virtual circle when the first arc is extended to set the virtual circle, and a bending angle (θ) between the clamp and a lower surface of the pressing part, to evaluate at least one of a strain (L) of the bent specimen, a folding stress ($\sigma_r$) applied to the bent specimen, and a folding modulus ($M_f$) of the bent specimen.

In an embodiment, the length L" may be represented by Equation 1:

$$L'' = \frac{\rho \pi \theta}{540} \qquad \text{[Equation 1]}$$

In an embodiment, the length L' may be represented by Equation 2:

$$L' = 2\rho \sin\frac{\theta}{6} \qquad \text{[Equation 2]}$$

In an embodiment, the strain (L) may be a parameter depending on only the bending angle (θ).

In an embodiment, the strain (L) may be represented by Equation 3:

$$\Delta L = \left( \frac{\pi\theta}{1080\sin\frac{\theta}{6}} - 1 \right) \times 100 \qquad \text{[Equation 3]}$$

In an embodiment, the folding stress ($\sigma_f$) may be represented by Equation 4:

$$\sigma_f = \frac{3y'L'F}{whd'^2} \qquad \text{[Equation 4]}$$

In an embodiment, in Equation 4, y' is a parameter considering stress asymmetry of a specimen at each point, F is a force of the pressing part pressing the specimen, w is a length directional width of the specimen, and d' a length of a second straight line connecting a halfway point of the first straight line with a halfway point of the first arc.

In an embodiment, the parameter y' may be represented by Equation 5:

$$y' = \frac{(10h)^2 \left(1 - \cos\frac{\theta}{6}\right)}{\rho^2 (1 - \cos 30°)} \qquad \text{[Equation 5]}$$

In an embodiment, the length d' may be represented by Equation 6:

$$d' = \rho\left(1 - \cos\frac{\theta}{6}\right) \qquad \text{[Equation 6]}$$

In an embodiment, the folding modulus ($M_f$) may be a parameter depending on the h, the $\rho$, and the bending angle $\theta$.

In an embodiment, the folding modulus ($M_f$) may be represented by Equation 7:

$$M_f = \frac{4.8 \times 10^4 hF \sin\frac{\theta}{6}}{w\rho^3 \left(1 - \cos\frac{\theta}{6}\right)} \times \left( \frac{\sin\frac{\theta}{6}}{\pi\theta - 1080\sin\frac{\theta}{6}} \right) \qquad \text{[Equation 7]}$$

In an embodiment, the bending angle $\theta$ may be greater than about 0 degree and equal to or less than about 180 degrees.

Flexural property of a material may be quantitatively evaluated by a simple method.

BRIEF DESCRIPTION OF THE DRAWINGS

The above and other embodiments, advantages and features of this disclosure will become more apparent by describing in further detail embodiments thereof with reference to the accompanying drawings, in which.

DETAILED DESCRIPTION

Figure 1:
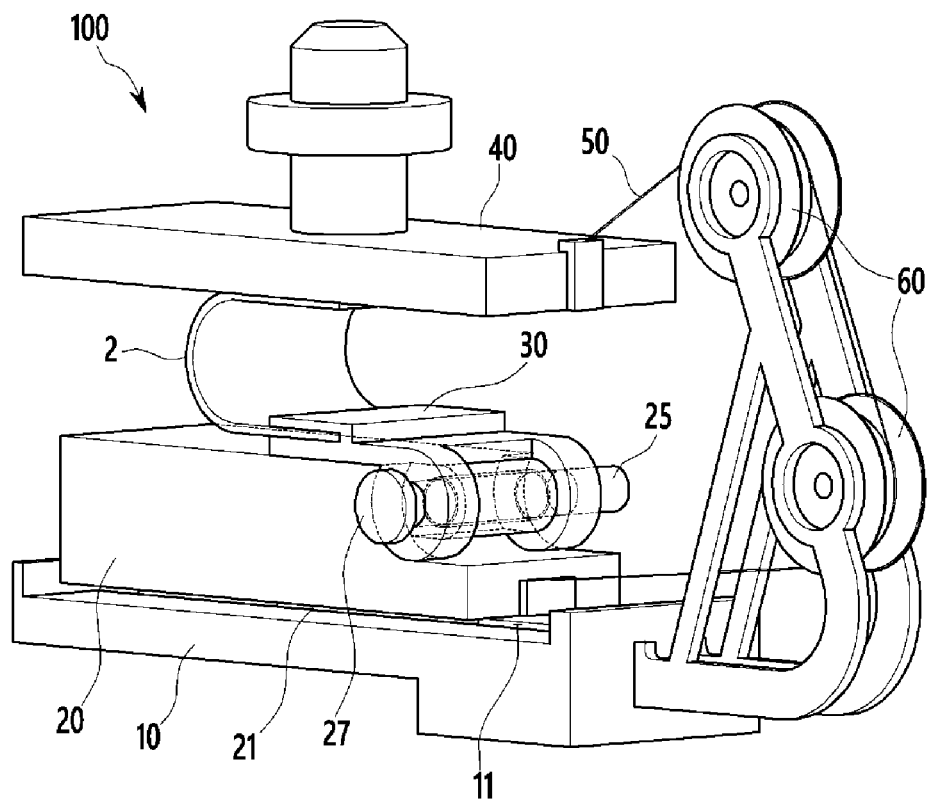
FIG. 1 is a perspective view of an embodiment of an evaluating device of a flexural property.

Hereinafter, embodiments will hereinafter be described in detail, and may be easily performed by those who have common knowledge in the related art. However, this disclosure may be embodied in many different forms and is not to be construed as limited to the embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the disclosure, the term of a flexural property refers to a property of a material measured when the material is bent or folded, and the property may include, for example, a folding stress, a bending modulus of elasticity, a strain of the material, and a strained amount, and the like.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. In an embodiment, when the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, when the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. In an embodiment, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the claims.

Hereinafter, the particular structure of the evaluating device of a flexural property according to an embodiment is described with reference to FIGS. 1 to 3.

FIG. 1 is a perspective view of an evaluating device of a flexural property according to an embodiment.

A device 100 for evaluating a flexural property according to an embodiment may bend or fold a specimen 2 to be evaluated to provide a predetermined angle between both ends of the specimen 2. Hereinafter, the various expressions relating to the deformation are unified with one term of "bending" for the convenience.

A shape and a material of the specimen 2 to be evaluated are not particularly limited as long as the specimen 2 may be bent or folded with fixing both ends of the specimen 2. In an embodiment, the specimen 2 may have a two-dimensional shape such as a film shape such as a thin film and a thick film, a sheet shape, or a plate shape, or may have a one-dimensional shape such as a fiber shape. In an embodiment, the material of the specimen 2 may include metal, plastic, ceramic, or a combination thereof, for example.

However, for describing the device 100 for evaluating a flexural property according to an embodiment, the specimen 2 is described having a film shape as shown in FIG. 1, for the convenience.

The device 100 for evaluating flexural property includes a holder 10, a body 20 disposed on the holder 10, a clamp 30 coupled to the body 20 and fixing one side of a specimen 2, and a pressing part 40 disposed over the clamp 30.

The holder 10 supports a lower part of the body 20 so that the body 20 is placed on an upper part of the holder 10. The holder 10 may have any shapes without particular limitations as long as it is longitudinally extended along with a length direction (e.g., a horizontal direction in FIG. 2). In an embodiment, the holder 10 may have, for example, a stick shape or a bar shape, or the similar shape thereto, for example.

The holder 10 may include a fixing part (not shown) on one side thereof so that the holder 10 is positioned or fixed on a ground, a wall surface, or the like.

A guide groove 11 may be defined in the upper surface of the holder 10 along with a length direction of the holder 10. The guide groove 11 guides the body 20 so that the body 20 may be slid along with a length direction of the holder 10. The shape of the guide groove 11 is not particularly limited as long as the guide groove 11 may accommodate a part of the body 20 and guide the body 20, and the shape of the guide groove 11 may include, for example, a variety of groove shapes such as U-shaped groove, V-shaped groove, W-shaped groove, for example.

Figure 2:
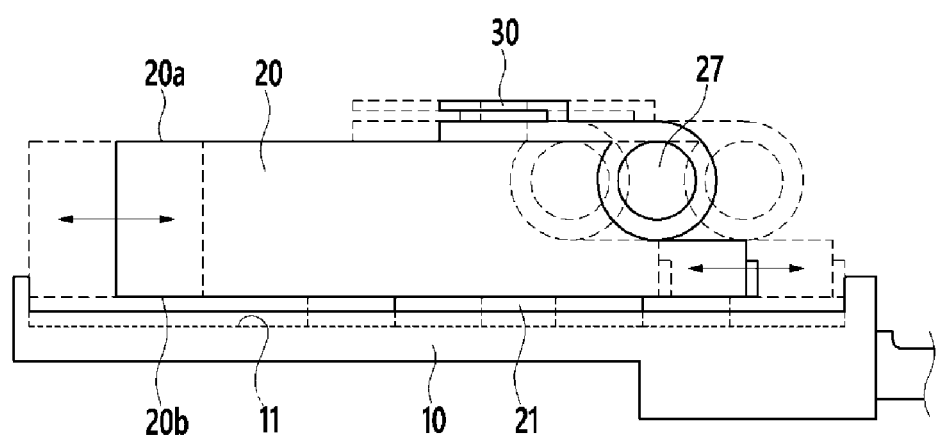
FIG. 2 is a front view showing an embodiment of an operation of sliding a body on a support member in a device for evaluating flexural property.

FIG. 2 is a view showing an operation of sliding a body of the device for evaluating flexural property according to an embodiment on the support member.

The body 20 is disposed on the holder 10 so that it may be slid along with a length direction of the holder 10, as shown in FIG. 2. Thus, the position of the body 20 may be adjusted depending upon a variety of shapes (length, thickness, etc.) of the specimen 2 to be evaluated. In addition, by sliding the body 20, the angle range of bending the specimen 2 (also referred to as "bending angle" to be described later) may be widely adjusted.

The controlling the bending angle by sliding the body 20 will be described in further detail with a method of evaluating flexural property which will be described later.

The body 20 includes an upper surface 20a facing the pressing part 40 and a lower surface 20b facing the holder 10. A movement member 21 is disposed (e.g., mounted) on the lower surface 20b to be accommodated in the guide groove 11. A kind of the movement member 21 is not particularly limited as long as the movement member 21 may slide the body 20 into the holder 10.

In an embodiment, the movement member 21 may be a means such as a wheel for lowering friction force between the body 20 and the holder 10, or a protruding portion protruded from the lower surface of the body 20 to be inserted into the guide groove 11 while having a lower friction coefficient than the friction coefficient of the guide groove 11.

The clamp 30 may be coupled to be rotated on the body 20. The clamp 30 clamps and fixes one side of the specimen 2 so as not to be separated from the device 100 for evaluating flexural property. The clamp 30 may be rotated in a predetermined angle with reference to the body 20 so that the bending degree of the bent specimen 2 may be controlled, as shown in FIG. 1.

Figure 3:
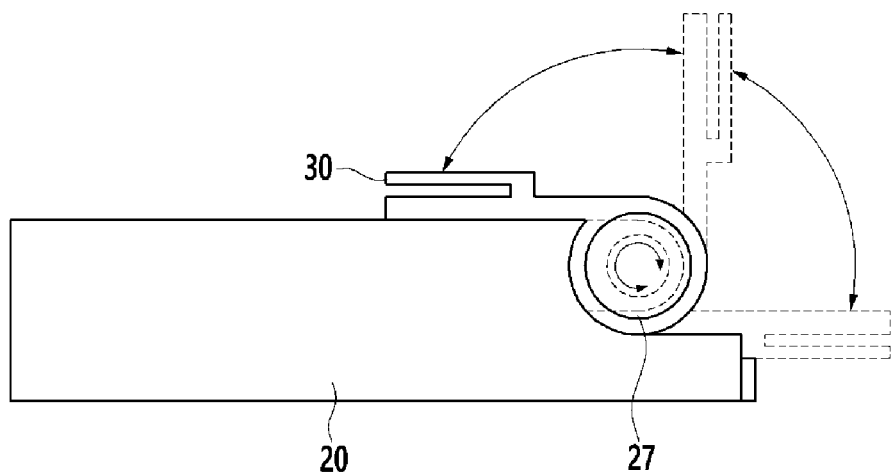
FIG. 3 is a front view showing an embodiment of an operation of rotating a clamp on a body in a device for evaluating flexural property.

FIG. 3 is a front view showing an operation of rotating a clamp on a body of a device for evaluating flexural property.

Referring to FIG. 3, an angle between the clamp 30 and the body 20 may be 0 degree to about 180 degrees in an embodiment. In other words, in an embodiment, as the clamp 30 may be rotated on the body in a relatively wide range, the bent angle range of the bent specimen 2 (also referred to as "bending angle" to be described later) may be widely controlled. The controlling the bending angle using a rotation of the clamp 30 will be described in further detail through a method of evaluating flexural property evaluation which will be described later.

The clamp 30 may be rotated by a rotation axis 25 passing through the body 20 and the clamp 30. According to an embodiment, the elongation direction of the rotation axis 25 may be different from the length direction of the holder 10. According to an embodiment, the elongation direction of the rotation axis 25 may be perpendicular to the length direction of the holder 10, as shown in FIG. 1. Thereby, the clamp 30 may be folded to be laid down on the body 20 along with a length direction of the body 20 or may be unfolded to be rotated until a predetermined angle between the clamp 30 and the upper side of the body 20 becomes about 180 degrees.

A manipulating dial 27 may be combined at one end of the rotation axis 25. The manipulating dial 27 may be rotated together with the rotation axis 25 and the clamp 30. Thereby, a user may more precisely control a rotating operation and position of the clamp 30 by the manipulating dial 27. The manipulating dial 27 may be combined at only one end of the rotation axis, or may be paired and combined at both ends of the rotation axis.

One surface of the manipulating dial 27 may be indicated with a scale, a signal, or the like so that a user may monitor how the rotation axis 25 is rotated. However, an embodiment is not necessarily limited thereto, but the scale, the signal or the like may be marked on the body 20 adjacent to the manipulating dial 27, or may be marked on both the manipulating dial 27 and the body 20.

The pressing part 40 is disposed over the clamp 30. The pressing part 40 may be moved nearer to the clamp 30 or farther from the clamp 30. According to an embodiment, one side of the specimen 2 is fixed by the clamp 30, an opposite side of specimen 2 which is opposite to the one side and not fixed is bent to be disposed upper than the one side of the specimen 2, and then the opposite side of the specimen 2 is pressed by the pressing part 40. Thereby, one side of the specimen 2 is fixed by the clamp 30, and the opposite side of the specimen 2 is fixed by the pressing part 40, then the specimen 2 is bent as shown in FIG. 1.

The lower surface of the pressing part 40 facing the clamp 30 may be flat. Thereby, a part of the opposite side of the specimen 2 may contact the lower surface of the pressing part 40 to be flatly pressed without a wave. In addition, as the lower surface of the pressing part 40 and a part of the opposite side of the specimen which contact the lower surface of the pressing part 40 are pressed flat, it may be estimated as a standard for measuring a bent angle (also referred to as "bending angle" which will be described later) of the specimen 2.

According to an embodiment, the pressing part 40 may include a pressing plate facing the clamp and a transporting part connected with the pressing plate and controlling a distance between the pressing plate and the clamp. In an embodiment, the transporting part includes, for example, a transducer such as a hydraulic actuator, a rack/pinion actuator, or a linear variable displacement transducer ("LVDT"), so as to linearly transport the pressing plate. Thereby, the transporting part may control the position of the pressing part 40 and fix the pressing part 40 without a complicated operation.

However, the pressing part 40 according to an embodiment may have any shapes as long as the surface of the pressing part 40 facing the clamp 30 is flat, and the pressing part 40 may be moved nearer to or farther from the clamp 30 where the movement includes one-dimensional movement such as linear transport, two-dimensional movement, or three-dimensional movement.

The device 100 for evaluating flexural property according to an embodiment may further include a wire 50 and a pulley 60.

The wire 50 may be connected with each of the body 20 and the pressing part 40, as shown in FIG. 1. In other words, one movement of either the body 20 or the pressing part 40 may be co-worked with the other movement through the wire 50.

The pulley 60 may be spaced from the holder 10, the body 20, and the pressing part 40. The pulley 60 may be wound with a wire 50. Thereby, the user may operate a pulley 60 to conveniently control the positions of the body 20 and the pressing part 40.

When using the pulley 60, the bent part of the specimen 2 may be controlled to be disposed in a predetermined position of the device 100 for evaluating flexural property without being separated from the pressing part 40 or the body 20. In other words, as the pressing part 40 is getting down, the position of the bending part of the specimen 2 may be shifted to one direction of right or left from the position of the initial bending part. However, as the position of the body 20 and the pressing part 40 may be continuously controlled by the pulley 60 according to an embodiment, the pulley 60 may control to dispose the bending part of the specimen 2 in a predetermined position without being influenced by pushing down the pressing part 40.

When the material is folded or bent, American Society for Testing Materials ("ASTM") D790 or the like has been known as a general method of measuring flexural property of the bending region.

In a case of ASTM D790, the flexural property of a material is evaluated through a three-points bending test and a four-points bending test. In this case, both ends of the rod-shaped specimen are positioned on two regions spaced from each other in a predetermined distance, and the specimen is pressed in a vertical direction to the center part of the specimen in a constant speed until the specimen is broken out to measure a folding stress and a strain.

However, the general method is limited to evaluate the material having a millimeter-scaled thickness and also having a relatively strong hardness. In the case of a material having a nanometer to micrometer-scaled thickness or having a ductility, the general method is difficult to be applied since the weight control is difficult and the measurement accuracy is remarkably deteriorated.

In addition, the general method may not widely control the degree of bending the material (also referred to as "bending angle" which will be described later), so the bending property of the specimen may be not accurately measured according to the various bending angles, particularly, the bending property of the specimen may not be measured in the case when the material is folded over (i.e., the case that "bending angle" is 180 degrees).

However, in the device 100 for evaluating flexural property according to an embodiment, the body 20, the clamp 30, and the pressing part 40 are precisely controlled so that they are independently operated, or some of them are co-worked with each other. Thereby, the load applied to the specimen 2 may be precisely controlled.

Thus, the device 100 for evaluating flexural property according to an embodiment has a high measurement accuracy and may easily measure flexural property of a material having a nanometer to micro scaled thickness or having the ductility as well as the conventional hard material having a millimeter-scaled thickness.

In addition, the device 100 for evaluating flexural property according to an embodiment very widely rotates the clamp 30, so the specimen 2 may be bended in a variously ranged bending angle. That is, the device 100 for evaluating flexural property according to an embodiment may accurately measure the bending property of the specimen depending upon the various bending angles.

Hereinafter, a method for evaluating flexural property of the specimen using the device for evaluating flexural property is described with reference to FIGS. 4 to 11.

Figure 4:
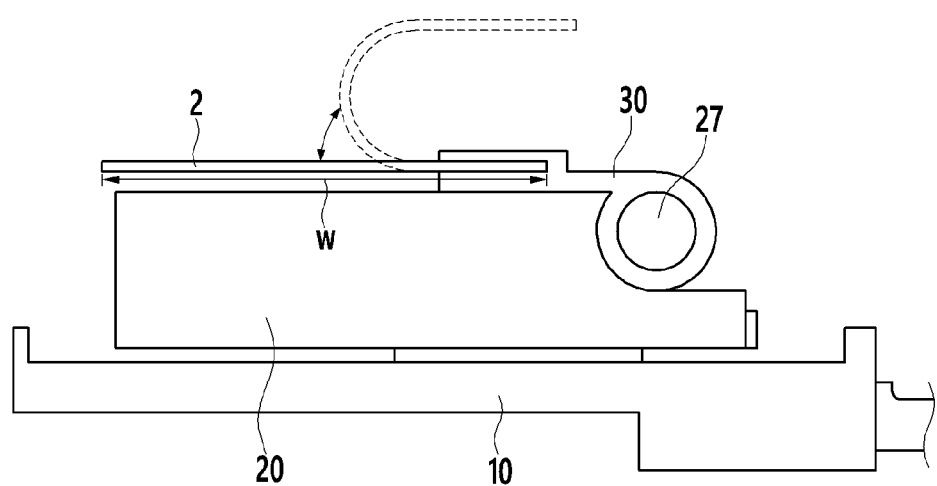
FIGS. 4 to 6 are front views sequentially showing an embodiment of a method of evaluating flexural property using the device for evaluating flexural property.
Figure 5:
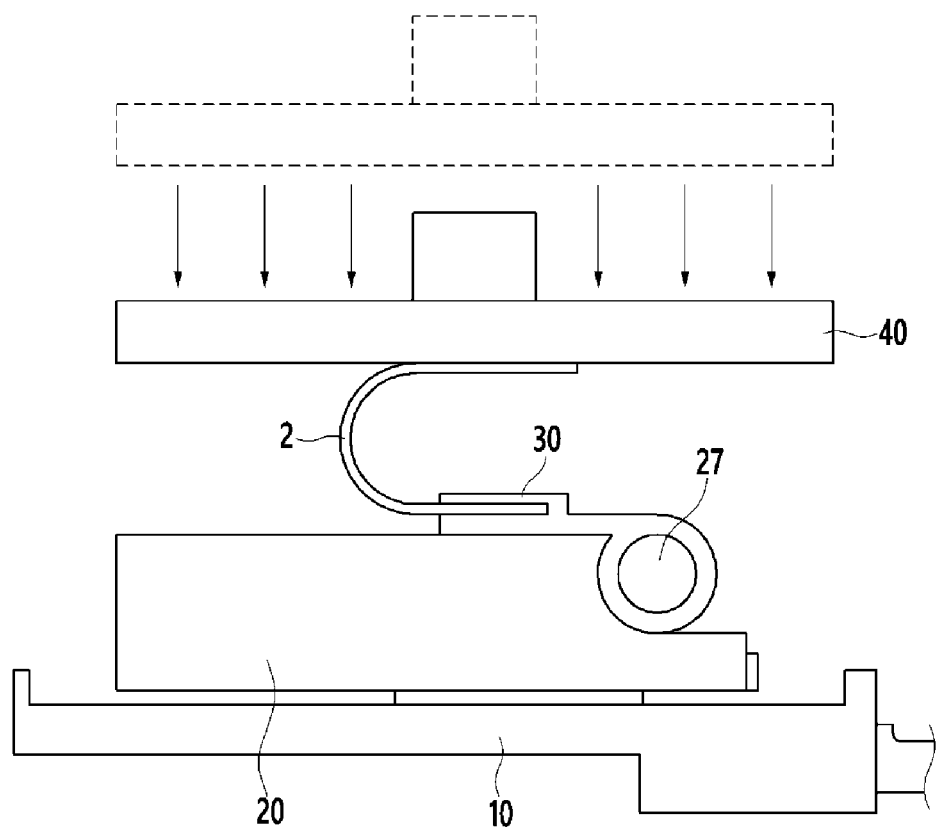
Figure 6:
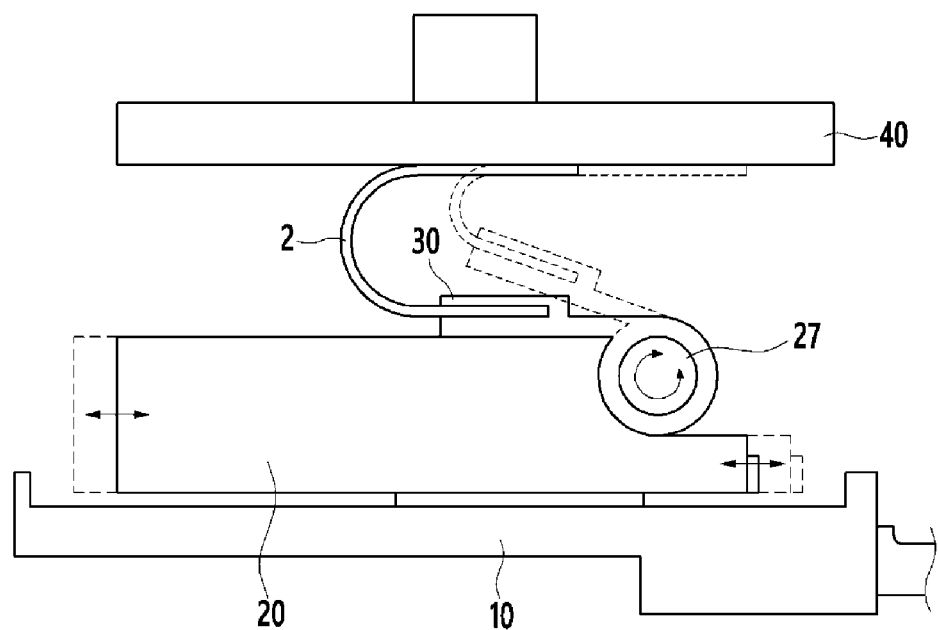

FIGS. 4 to 6 are front views sequentially showing a method for evaluating flexural property using the device for evaluating flexural property according to an embodiment.

First, a position of the specimen 2 is fixed by clamping one side of the specimen 2 by a clamp 30. In this case, a pressing part 40 is positioned upper than the opposite side of the bent specimen 2.

Then, the specimen 2 is bent to have the shape shown with the dotted line in FIG. 4 so that the opposite side of the specimen 2 is positioned upper than the one side of the clamped specimen 2.

Then, as shown in FIG. 5, the pressing part 40 is moved toward the clamp 30, so the opposite side of the bent specimen 2 is pressed and fixed. The specimen 2 fixed by the pressing part 40 may maintain the shape shown in FIG. 5. A part of the opposite side of the specimen 2 contacts the lower surface of the pressing part 40 and is disposed parallel to the lower surface of the pressing part 40.

Then, as shown in FIG. 6, the bent angle of the specimen 2 may be variously controlled by sliding the body 20 on the holder 10 or by adjusting the rotation position of the clamp 30 through the manipulating dial 27.

According to an embodiment, the bent angle of the specimen 2, which is the bending angle (θ) of the specimen 2, means an angle between the clamp 30 and the lower surface of the pressing part 40. Using the device 100 for evaluating flexural property according to an embodiment, the bending angle (θ) may be adjusted, for example, from 0 degree to about 180 degrees, for example, greater than 0 degree and less than or equal to about 180 degrees.

Figure 7:
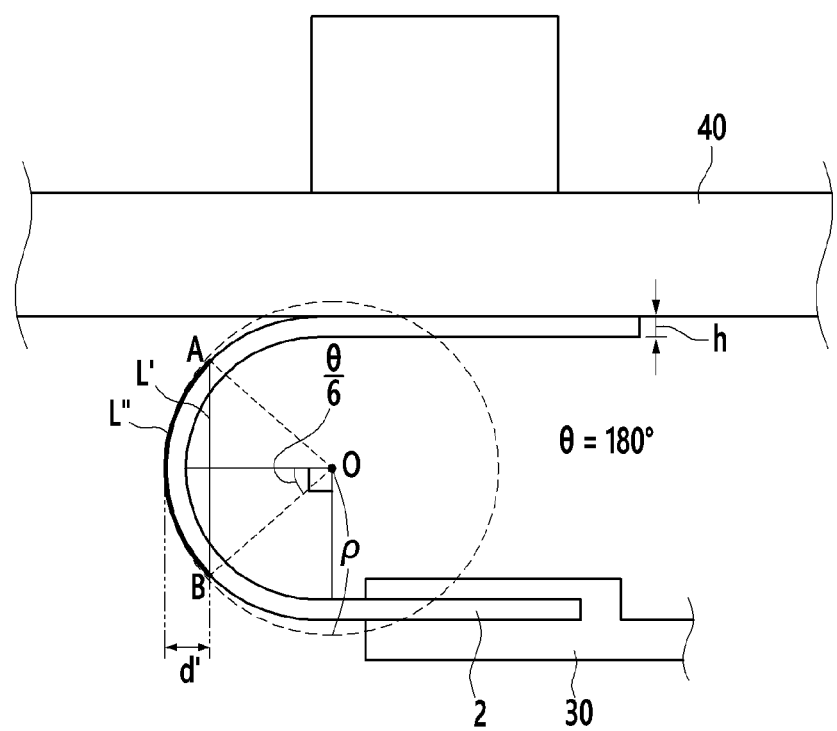
FIG. 7 is a front view showing the case that a bending angle ($\theta$) is about 180 degrees between the clamp and the pressing part in FIG. 6.
Figure 8:
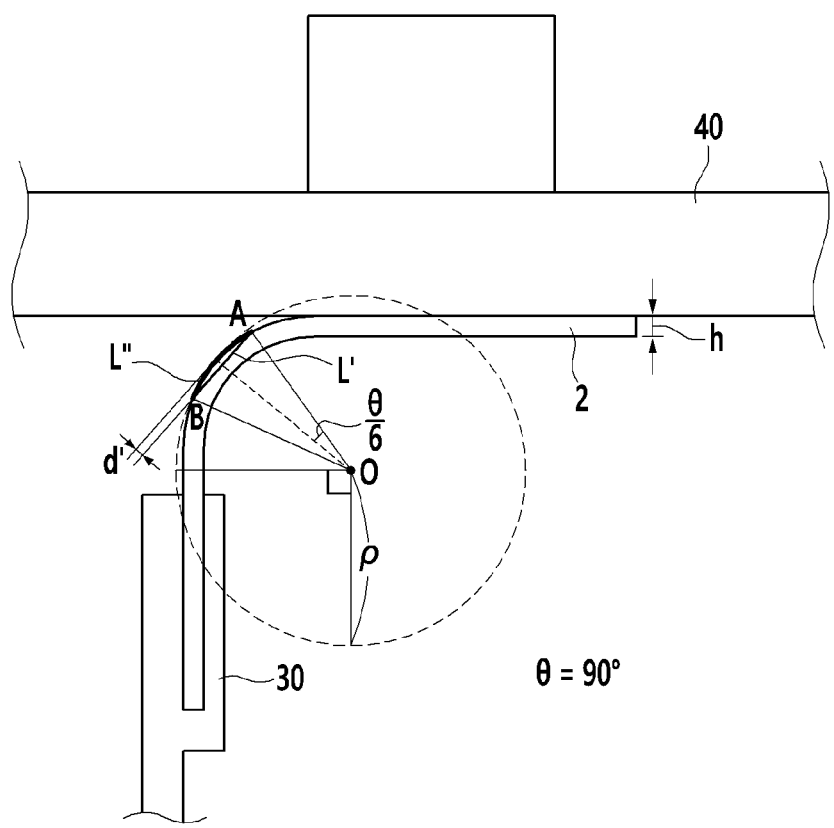
FIG. 8 is a front view showing the case that a bending angle ($\theta$) is about 90 degrees between the clamp and the pressing part in FIG. 6.
Figure 9:
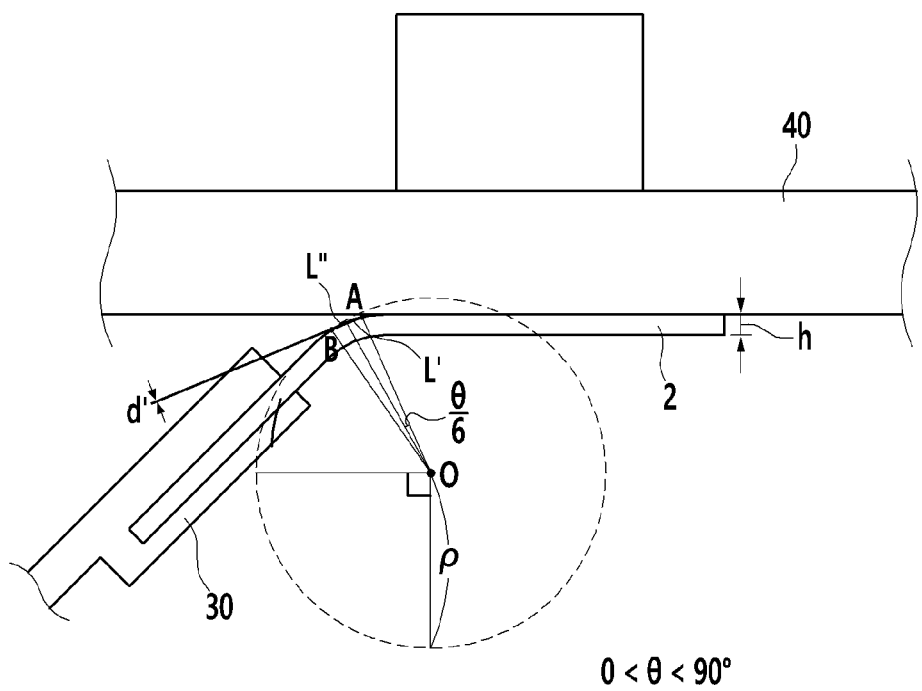
FIG. 9 is a front view showing the case that a bending angle ($\theta$) is an acute angle between the clamp and the pressing part in FIG. 6.
Figure 10:
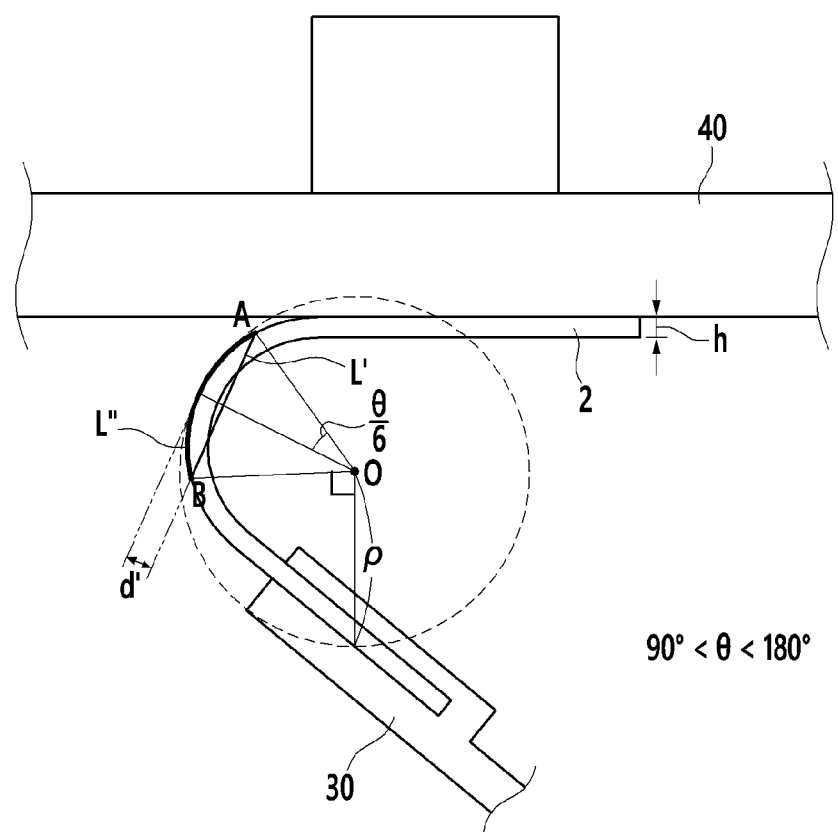
FIG. 10 is a front view showing the case that a bending angle ($\theta$) is an obtuse angle between the clamp and the pressing part in FIG. 6.

FIG. 7 is a front view showing a case that a bending angle (θ) between the clamp and the pressing part is about 180 degrees in FIG. 6, FIG. 8 is a front view showing a case that a bending angle (θ) is about 90 degrees, FIG. 9 is a front view showing a case that a bending angle (θ) is an acute angle, and FIG. 10 is a front view showing a case that a bending angle (θ) is an obtuse angle.

In other words, as the body 20 and the clamp 30 are moved as shown in FIG. 6, the specimen 2 is adjusted to provide a variety of bending angles (θ) within a range from 0 degree to about 180 degrees as shown in FIGS. 7 to 10.

Then, for the specimen 2 having a variety of bending angles (θ) as shown in FIGS. 7 to 10, a length (L″) of a first arc connecting different first and second points A and B applied with a principal stress corresponding to a half of the maximum principal stress applied to the bent specimen 2 is measured, a length (L′) of a first straight line connecting the first and second points A and B is measured, a virtual circle (dotted circle shown in FIGS. 7 to 10) is determined by extending the first arc to set a shape of circle, and then a curvature radius (ρ) of the virtual circle is calculated.

Then, by a thickness (h) of the specimen 2 in addition to the bending angle (θ), the length (L″) of the first arc, the length (L′) of the first straight line, and the curvature radius (ρ), a strain (L) of the bent specimen 2, a folding stress ($\sigma_f$) applied to the bent specimen 2, and a folding modulus ($M_f$) of the bent specimen 2 may be each evaluated.

In an embodiment, the length (L″) of the first arc corresponds to a length of the specimen 2 deformed by the bending. That is, it is because the specimen 2 is sharply deformed as going nearer to the bent center from the first and second points A and B where are applied with the principal stress corresponding to the half of the maximum principal stress, and the specimen 2 is not or little deformed in the other regions where are applied with the principal stress corresponding to less than the half of the maximum principal stress.

The length (L″) of the first arc may be a parameter for the bending angle (θ) and the curvature radius (ρ) of the virtual circle. According to Mohr's circle, each angle between a line extended to the center of the bent specimen 2 from the center O of the virtual circle and a line extended to each of the first and second points A and B from the center O of the virtual circle is θ/6. Thus the length (L″) of the first arc may be represented by Equation 1:

$$L'' = \frac{\rho \pi \theta}{540}$$ [Equation 1]

According to an embodiment, the length (L') of the first straight line corresponds to the initial length of the specimen 2, which is the shortest distance connecting the first and second points A and B. The length (L') of the first straight line may be a parameter for the bending angle (θ) and the curvature radius (ρ) of the virtual circle, as in the length (L") of the first arc, and more particularly, the length (L') may be represented by Equation 2:

$$L' = 2\rho \sin\frac{\theta}{6} \quad \text{[Equation 2]}$$

According to an embodiment, the stain (L) of the bent specimen 2 refers to an elongated ratio by bending the specimen 2 and may be calculated using the length (L") of the first arc and the length (L') of the first straight line.

The strain (L) of the specimen 2 may be calculated using the general formula for strain: "(length of specimen deformed by bending−initial length of specimen)/initial length of specimen."

The strain (L) of the specimen 2 may be represented by Equation 3:

$$\Delta L = \left(\frac{\pi\theta}{1080\sin\frac{\theta}{6}} - 1\right) \times 100 \quad \text{[Equation 3]}$$

Referring to Equation 3, it is confirmed that the strain (L) of the specimen may be a parameter not dependent upon the thickness (h) of the specimen, etc., but dependent upon the bending angle (θ).

According to an embodiment, a folding stress (σf) applied to the bent specimen 2 may be generalized using a stress of the first and second points A and B where the principal stress is equivalent to the shearing stress according to Mohr's circle. More particularly, the folding stress (σf) may be represented by Equation 4:

$$\sigma_f = \frac{3y'L'F}{whd'^2} \quad \text{[Equation 4]}$$

In Equation 4, y' is a parameter considering stress asymmetry of a specimen 2 at each point, F is a force of the pressing part 40 pressing the specimen 2, w (refer to FIG. 4) is a length direction width of the specimen 2, and d' is a length of a second straight line connecting a halfway point of the first straight line with a halfway point of the first arc.

In order to generalize the folding stress (σf), a correction parameter is desired considering a thickness (h) (refer to FIGS. 7-10) of the specimen 2, a folding moment of the bent specimen 2, a moment of inertial, positional information of the first and second points A and B according to Mohr's circle, positional information of a predetermined position according to Mohr's circle, and a positional factor of the first and second positions or the like.

According to an embodiment, using y' which is a parameter considering the stress asymmetry at each point of the specimen, the folding stress (σf) at each point of the specimen may be calculated.

More particularly, supposing that the curvature is increased as much as the curvature radius is less than the half of the initial length of the specimen, the stress asymmetric effect when the specimen is bent at 180 degrees is linearly proportional to 10 h/ρ, and the stress is proportional to (10 h/ρ)². The stress asymmetry is proportional to the bending angle and has the maximum value at a bending angle of 180 degrees and the minimum value at a bending angle of 0 degree, and a ratio according to Mohr's circle is represented by (1−cos θ/6)/(1−cos 30°). Thereby, considering the relationship between the stress and the bending angle, a parameter of y' may be calculated.

The y' may be represented by Equation 5:

$$y' = \frac{(10h)^2\left(1-\cos\frac{\theta}{6}\right)}{\rho^2(1-\cos 30°)} \quad \text{[Equation 5]}$$

According to an embodiment, d' is a parameter showing how the position of the deformed specimen 2 is deflected, respecting to the initial position of the specimen 2. In other words, d' refers to deflection of the deformed specimen 2. More particularly, d' may be represented by Equation 6:

$$d' = \rho\left(1 - \cos\frac{\theta}{6}\right) \quad \text{[Equation 6]}$$

In an embodiment, a folding modulus (Mf) of the specimen may be calculated using the calculated strain (L) and folding stress (σf) of the specimen. The folding modulus (Mf) is obtained by dividing the folding stress (σf) by the strain (L) of the specimen. Summarizing the aforementioned features, the folding modulus (Mf) may be represented by Equation 7:

$$M_f = \frac{4.8 \times 10^4 hF\sin\frac{\theta}{6}}{w\rho^3\left(1-\cos\frac{\theta}{6}\right)} \times \left(\frac{\sin\frac{\theta}{6}}{\pi\theta - 1080\sin\frac{\theta}{6}}\right) \quad \text{[Equation 7]}$$

According to an embodiment, the folding modulus (Mf) of the specimen may be defined by a parameter for the thickness (h) of the specimen, the curvature radius (ρ) of the virtual circle, and the bending angle (θ), as in Equation 7.

Figure 11:
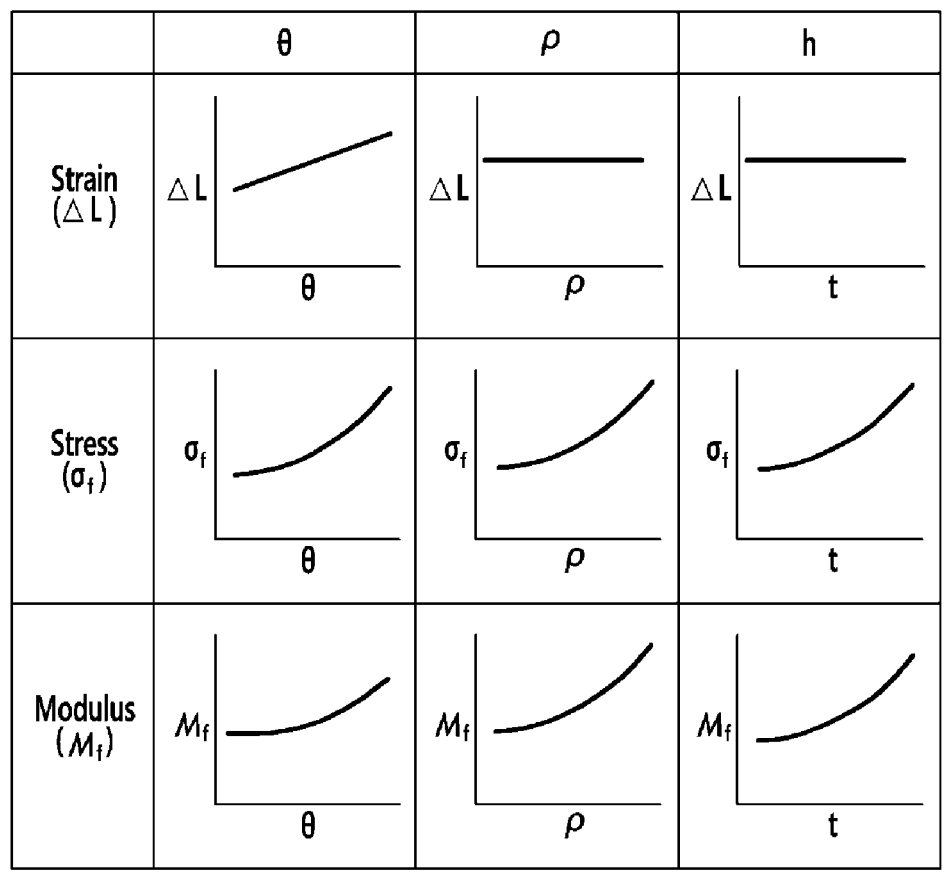
FIG. 11 is a diagram showing relationships of each of a strain (L) of the bent specimen, a folding stress ($\sigma_f$) applied to the bent specimen, and a folding modulus ($M_f$) of the bent specimen with respect to each of a bending angle ($\theta$), a curvature radius ($\rho$) of a virtual circle, and a thickness (h) of the specimen.

FIG. 11 is a view showing relationships between each of a bending angle (θ), a curvature radius (ρ) of the virtual circle virtual with the bent specimen, and a thickness (h) of the specimen and each of a strain (L) of the bent specimen, a folding stress (σf) applied to the bent specimen, and a folding modulus (Mf) of the specimen in a device for evaluating flexural property according to an embodiment.

Referring to FIG. 11, it is confirmed that the strain (L) of the specimen is dependent upon only the bending angle (θ) and is independent from the curvature radius (ρ) of the virtual circle or the thickness (h) of the specimen. However, it is confirmed that the folding stress (σf) is dependent upon the curvature radius (ρ) and the bending angle (θ) of the virtual circle by L' and d' as shown in Equation 5, and dependent upon the thickness (h) of the specimen by y'. Thus, it is confirmed that the folding modulus (Mf) of the specimen is dependent upon all of the bending angle (θ), the curvature radius (ρ) of the virtual circle, and the thickness (h) of the specimen.

According to an embodiment, the method of evaluating flexural property may evaluate flexural property of a material having a nanometer to micro-scaled thickness or having ductility, which was used to be hardly evaluated by the conventional method, and also may evaluate flexural property of the specimen at each bending angle while adjusting the bending angle (θ) in a wide range. That is, according to an embodiment, a method of evaluating flexural property may evaluate flexural property of the various materials so may be quantized and standardized.

Hereinafter, the measuring and the evaluating properties of various materials are described using an evaluating device of a flexural property according to an embodiment with Examples. These examples, however, are not in any sense to be interpreted as limiting the scope of the disclosure.

Evaluation 1—Correlation Between Curvature Radius (ρ) of Virtual Circle and Force Applied to Specimen:

One side of polyethylene terephthalate ("PET") film having a thickness of about 200 μm is fixed by a clamp, and the PET film is bent so that the opposite side of the PET film is positioned upper than the fixed one side of the PET film, and then a pressing part is pushed down to press the opposite side of the PET film. Then, the positions of the clamp and the body are adjusted to provide a bending angle of 180 degrees.

Figure 12:
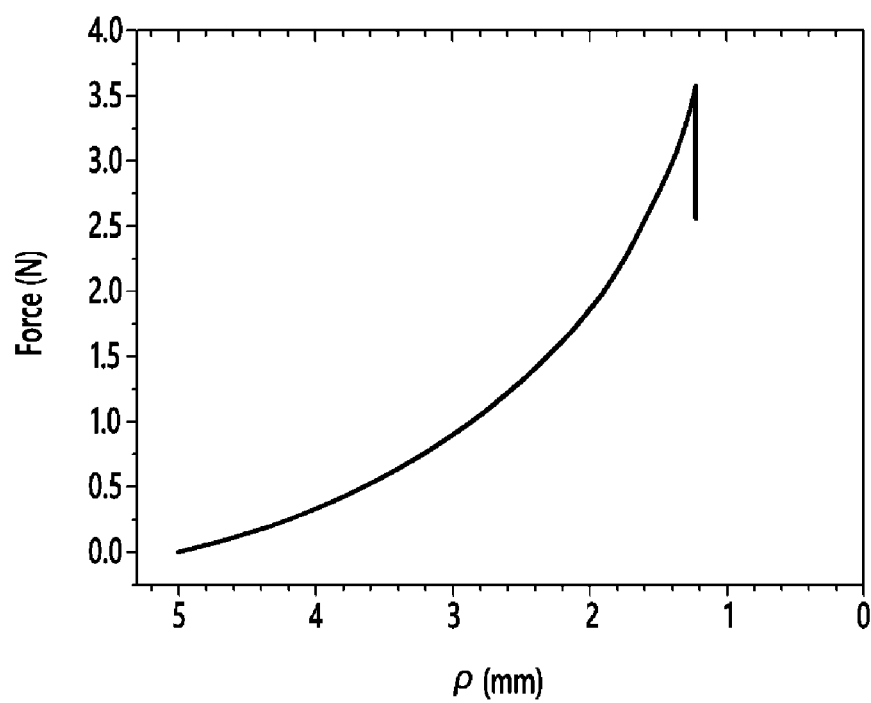
FIG. 12 is a graph showing an embodiment of force applied to the specimen with respect to a curvature radius ($\rho$) of a virtual circle when a polyethylene terephthalate film having a thickness of about 200 micrometers ($\mu$m) is bent in a bending angle 180 degrees by the device for evaluating flexural property.

Then, while the opposite side of the PET film is pressed using the pressing part, a correlation between a curvature radius (ρ) of an virtual circle and a force in terms of newton (N) applied to the specimen is measured, and the results are shown in graph of FIG. 12.

Referring to FIG. 12, it is confirmed that the gap between the one side and the opposite side of the PET film is getting narrower as increasing the force applied to the specimen, so it is confirmed that the curvature radius (ρ) is also getting decreased. However, it is confirmed that the force applied to the specimen is rapidly decreased at a point of a curvature radius (ρ) of about 1.2 millimiters (mm).

In other words, it is understood that the plastic deformation such as damage of the PET film is occurred at a curvature radius (ρ) of less than or equal to about 1.2 mm when the PET film is completely folded over (when the bending angle is adjusted to be about 180 degrees).

Thereby, when the PET film is used under the condition of bending the same at a bending angle of about 180, a curvature radius (ρ) of the virtual circle is adjusted to greater than or equal to about 1.2 mm, for example, greater than or equal to about 1.5 mm, for example, greater than or equal to about 2.0 mm.

Figure 13:
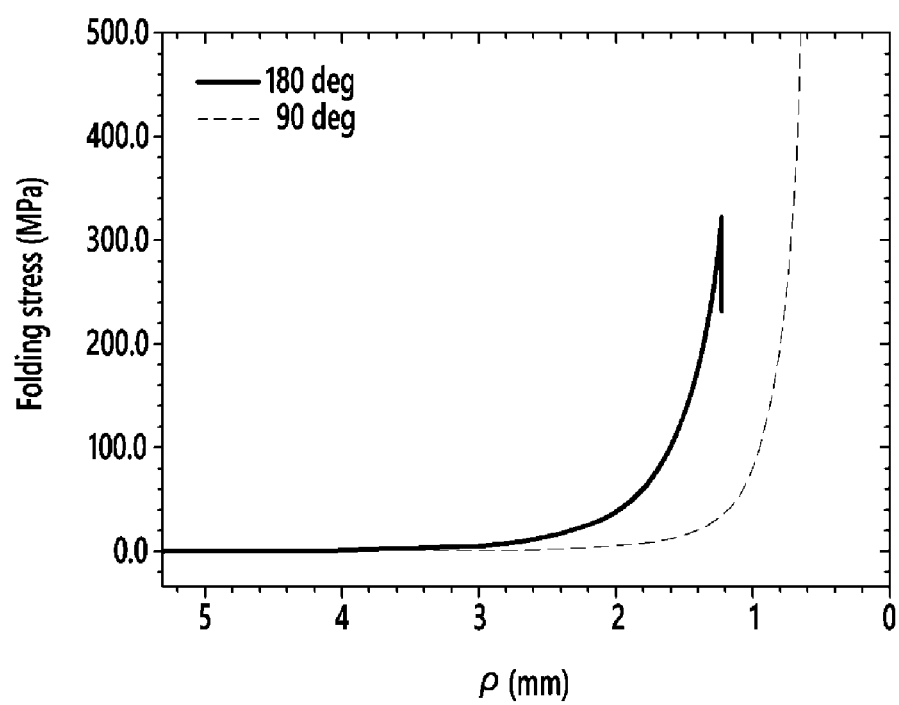
FIG. 13 is a graph showing an embodiment of a folding stress applied to the specimen with respect to a curvature radius ($\rho$) of a virtual circle when a polyethylene terephthalate film having a thickness of about 200 $\mu$m is bent in each bending angle of 180 degrees or about 90 degrees by the device for evaluating flexural property.

Evaluation 2—Correlation Between Curvature Radius (ρ) of Virtual Circle and Folding Stress (σ$_f$) and Between Curvature Radius (ρ) of Virtual Circle and Folding Modulus (M$_f$):

The correlation between the curvature radius (ρ) of the virtual circle obtained from Evaluation 1 and the force applied to the specimen is entered into Equation 4, so the correlation between the curvature radius (ρ) of the virtual circle and the folding stress (σ$_f$) is calculated, and the results are shown in FIG. 13.

Figure 14:
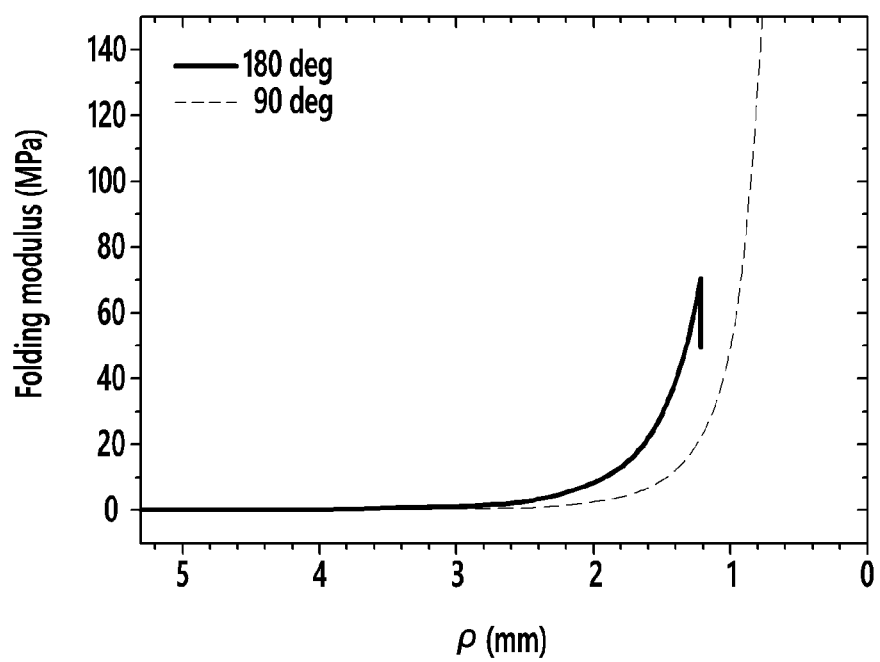
FIG. 14 is a graph showing an embodiment of a folding modulus of the specimen with respect to a curvature radius ($\rho$) of a virtual circle when a polyethylene terephthalate film having a thickness of about 200 $\mu$m is bent in each bending angle of 180 degrees or about 90 degrees by the device for evaluating flexural property.

The correlation between the curvature radius (ρ) of the virtual circle and the force applied to the specimen are entered into Equation 7, so the curvature radius (ρ) of the virtual circle and the folding modulus (M$_f$) are calculated, and the results are shown in FIG. 14.

The same process is performed once more, except that the bending angle is adjusted to about 90 degrees, and then the correlation between the curvature radius (ρ) of the virtual circle and the folding stress (σ$_f$) is calculated, and the results are shown in FIG. 13, and the curvature radius (ρ) of the virtual circle and the folding modulus (M$_f$) are calculated, and the results are shown in FIG. 14.

Referring to FIG. 13, under both conditions of the bending angle of 180 degrees and the bending angle of 90 degrees, it shows the tendency that the curvature radius (ρ) of virtual circle is gradually decreased as increasing the folding stress (of).

Under the condition of the bending angle of about 180 degrees, it is confirmed that the folding stress applied to the specimen begins to be slowly increased from a point where the curvature radius (ρ) is less than or equal to about 3 mm, and then the folding stress is rapidly increased from a point of less than or equal to about 2 mm, and the folding stress sharply decreased at a point of about 1.2 mm.

Under the condition of the bending angle of about 90 degrees, the folding stress is gradually increased from a point of less than or equal to about 2 mm, and the folding stress is sharply increased from a point of less than or equal to about 1.0 mm to the point of about 0.6 mm.

Under the condition of the bending angle of about 90 degrees, there is no region where the folding stress is rapidly decreased in a range of the folding stress from 0 megapascal (MPa) to 500 MPa. Thereby, it is understood that the condition of the bending angle of about 90 degrees is better than the condition of the bending angle of about 180 degrees when the lower curvature radius (ρ) condition is demanded.

Referring to FIG. 14, it is confirmed that graph outline showing the correlation between the curvature radius (ρ) of the virtual circle and the folding modulus (MO corresponds to the graph outline of FIG. 13. Thereby, it is confirmed that the strain (L) of the specimen is not related to the curvature radius (ρ) of the virtual circle.

Evaluation 3—Correlation Between Curvature Radius (ρ) of Virtual Circle and Folding Stress (σ$_f$) Depending Upon Thickness of Specimen and Between Curvature Radius (ρ) of Virtual Circle and Folding Modulus (M$_f$):

Each PET specimen having different thicknesses of about 200 micrometers (μm), about 125 μm, about 100 μm, about 75 μm, about 50 μm, and about 25 μm is prepared, and then a correlation between the curvature radius (ρ) of the virtual circle and the force applied to the specimen is obtained by the same method as in Evaluation 1. In this case, all the specimens are designated to have the bending angle of about 180 degrees.

Figure 15:
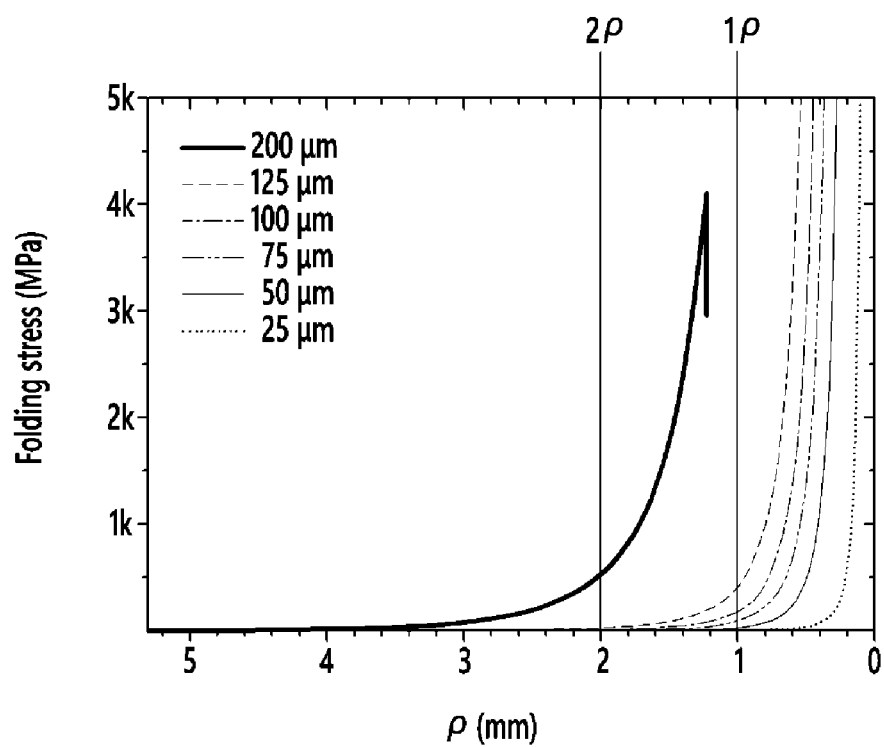
FIG. 15 is a graph showing an embodiment of a folding stress applied to the specimen with respect to a curvature radius ($\rho$) of a virtual circle when polyethylene terephthalate films having different thicknesses are bent in a bending angle of about 180 degrees using the device for evaluating flexural property.

Then, the obtained correlation between the curvature radius (ρ) of the virtual circle and the force applied to the specimen is entered into Equation 4, so the correlation between the curvature radius (ρ) of the virtual circle and the folding stress (σ$_f$) is calculated, and the results are shown in FIG. 15.

Figure 16:
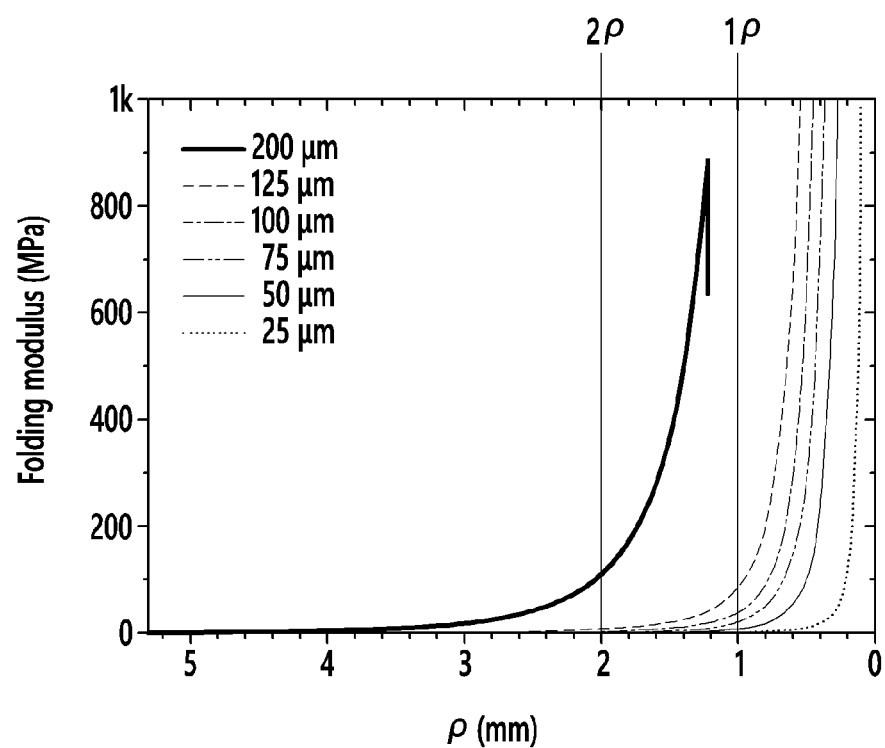
FIG. 16 is a graph showing an embodiment of a folding modulus of the specimen with respect to a curvature radius ($\rho$) of a virtual circle when polyethylene terephthalate films having different thicknesses are bent in a bending angle of about 180 degrees using the device for evaluating flexural property.

The obtained correlation between the curvature radius (ρ) of the virtual circle and the force applied to the specimen is substituted into Equation 7, so the curvature radius (ρ) of the virtual circle and the folding modulus (M$_f$) are calculated, and the results are shown in FIG. 16.

Referring to FIGS. 15 and 16, as the PET film has the thicker thickness, the folding stress and the folding modulus are going higher. This is estimated because the larger force is needed to bend the PET film having the thicker thickness.

Referring to FIGS. 15 and 16, as the PET film has thinner thickness, the curvature radius (ρ) of virtual circle corresponding to the same folding stress and the same folding modulus is going smaller. Thereby, when is used under the bending condition at a bending angle of about 180 degrees, as the PET film has the thinner thickness, the estimated range of the curvature radius (ρ) of the virtual circle may be wider.

As studied above, the device for evaluating flexural property according to an embodiment may easily evaluate the flexural property of the material which was difficult to be evaluated by the conventional evaluating device of a flexural property, and the flexural property of the specimen may be evaluated for each bending angle condition by adjusting the bending angle in the various range. That is, by the device for evaluating flexural property according to an embodiment, the flexural property of the various materials may be evaluated to be qualified and standardized.

While this disclosure has been described in connection with what is presently considered to be practical embodiments, it is to be understood that the disclosure is not limited to the disclosed embodiments, but, on the contrary, is intended to cover various modifications and equivalent arrangements included within the spirit and scope of the appended claims.

What is claimed is:

1. A device for evaluating flexural property comprising:
   a holder,
   a body disposed on the holder and capable of being moved along with a length direction of the holder,
   a clamp coupled to the body and capable of being rotated on the body and fixing a first side of a specimen to be evaluated,
   a pressing part which is disposed on the clamp, contacts and directly presses a second side of the specimen opposite to the first side and is disposed upper than the first side of the specimen to bend the specimen,
   a wire connected with each of the body and the pressing part, and
   a pulley wound with the wire.

2. The device of claim 1, further comprising:
   a rotation axis penetrating the body and the clamp and inserted through the body and the clamp; and
   a manipulating dial coupled to a terminal end of the rotation axis.

3. The device of claim 2, wherein an elongation direction of the rotation axis is different from the length direction of the holder.

4. The device of claim 1, wherein an angle between the clamp and the body is about 0 degree to about 180 degrees.

5. The device of claim 1, wherein the body is disposed to be slid along with the length direction of the holder.

6. The device of claim 5, wherein a guide groove is defined in an upper surface of the holder along with the length direction of the holder, and
   a movement member is disposed on a lower surface of the body to be accommodated in the guide groove.

* * * * *